United States Patent [19]
Jaeger et al.

[11] Patent Number: 5,397,337
[45] Date of Patent: Mar. 14, 1995

[54] METHOD AND APPARATUS FOR ARTIFICIALLY STIMULATING COUGH REFLEX

[75] Inventors: Robert J. Jaeger, Hinsdale; Elliot J. Roth, Northbrook, both of Ill.

[73] Assignee: Illinois Institute of Technology, Chicago, Ill.

[21] Appl. No.: 219,250

[22] Filed: Mar. 29, 1994

Related U.S. Application Data

[63] Continuation-in-part of Ser. No. 862,344, Apr. 2, 1992, Pat. No. 5,314,454.

[51] Int. Cl.⁶ .............................................. A61N 1/18
[52] U.S. Cl. .................................... 607/62; 607/65
[58] Field of Search ................................. 607/62, 65

[56] References Cited

U.S. PATENT DOCUMENTS

| | | |
|---|---|---|
| 4,147,171 | 4/1979 | Greene et al. |
| 4,155,366 | 5/1979 | Di Mucci |
| 4,459,989 | 7/1984 | Borkan |
| 4,895,154 | 1/1990 | Bartelt et al. |
| 5,048,523 | 9/1991 | Yamasawa et al. |
| 5,190,036 | 3/1993 | Linder |

OTHER PUBLICATIONS

Polatty, R. Crystal, M.D. et al., *Pulmonary Complications in the Spinal Cord Injury Patient*, Physical Medicine and Rehabilitation, vol. 1, No. 3, pp. 353–373, Aug. 1987.

Kirby, Nell A., R.N. et al., *An Evaluation of Assisted Cough in Quadriparetic Patients*, Archives of Physical Medicine & Rehabilitation, vol. 47, pp. 705–710, 1966.

Reines, H. David, M.D. et al., *Pulmonary Complications of Acute Spinal Cord Injuries*, Neurosurgery, vol. 21, No. 2, pp. 193–196-1987.

Braun, Sheldon R., M.D. et al., *Improving the Cough in Patients with Spinal Cord Injury*, American Journal of Physical Medicine, vol. 63, No. 1, pp. 1–10, 1984.

Glenn, William W. L. et al., *Twenty Years of Experience in Phrenic Nerve Stimulation to Pace the Diaphragm*, Pace, vol. 9, pp. 780–784, Nov.–Dec. 1986, Part I.

Peterson, D. K. et al., *Intramuscular Electrical Activation of the Phrenic Nerve*, IEEE Transactions on Biomedical Engineering, vol. BME-33, No. 3, pp. 342–351, Mar. 1986.

Geddes, L. A. et al., *Electroventilation*, American Journal of Emerg. Med., vol. 3(4) pp. 337–339, Jul. 1985.

Linder, S. H. M.D., *Abdominal Muscle FES to Enhance Cough in Spinal Cord Injury*, J. Am. Paraplegia Soc., vol. 13, No. 4, Oct. 1990.

Linder, S. H., M.D., *Use of Functional Electrical Stimulation Abdominal Binder to Enhance Cough In Quadriplegia*, Chest, vol. 100, No. 2, Supplement, p. 77S, Aug. 1991.

(List continued on next page.)

*Primary Examiner*—William E. Kamm
*Assistant Examiner*—Scott M. Getzow
*Attorney, Agent, or Firm*—Speckman, Pauley & Fejer

[57] ABSTRACT

A method and apparatus for eliciting a physiologically significant cough reflex, such as in a quadriplegic patient. The apparatus preferably has at least one pair of electrodes which are positioned about or near the abdominal muscles. The user generates an input signal. The input signal and a stimulus pulse signal are computed into an output signal. Prior to the delivery of the output signal, alerting signals are delivered to the user to alert the user of an upcoming cough and the onset of pulse electrical voltage to allow the user to engage appropriate volitional activity to optimally engage and complete the cough. The output signal is transformed into a pulse electrical voltage which is delivered across each pair of electrodes. Such pulse electrical voltage activates the lower motor neurons and thereby contracts the abdominal muscles to elicit a physiologically significant cough reflex. The pulse electrical voltage can be delivered at an optimum time, which can be calculated as a function of a physical and temporal status of the cough and a volitional activity by the user, in order to achieve a maximum air flow rate of the cough.

17 Claims, 3 Drawing Sheets

OTHER PUBLICATIONS

Traver, Gayle A., R.N., *Ineffective Airway Clearance: Physiology and Clinical Application, Dimensions of Critical Care Nursing,* vol. 4, pp. 198–208, 1985.

Estenne, Marc, M.D., et al., *Cough in Tetraplegic Subjects: An Active Process,* Annals of Internal Medicine, vol. 112, pp. 22–28, 1990.

Peterson, D. K., et al., *Electrical Activation of Respiratory Muscles by Methods Other than Phrenic Nerve Cuff Electrodes,* Diaphragm Stimulation Symposium at Cardiostim '88, Jun. 15–18, 1988, Pace, vol. 12, May 1989, pp. 854–860.

Steven H. Linder, "Functional Electrical Stimulation to Enhance Cough in Quadriplegia", Chest, 103, 1, Jan. 1993.

METHOD AND APPARATUS FOR ARTIFICIALLY STIMULATING COUGH REFLEX

This invention was made as a result of work under Research Grant H133N00008, granted by the United States Department of Education.

CROSS-REFERENCE TO RELATED APPLICATION

This is a continuation-in-part patent application of U.S. patent application having Ser. No. 07/862,344, filed Apr. 2, 1992, now U.S. Pat. No. 5,314,454.

BACKGROUND OF THE INVENTION

1. Field of the Invention

This invention relates to a method and apparatus for artificially and electrically stimulating cough reflex for improving the life span of individuals with higher level spinal cord injuries, and perhaps other individuals with impaired cough. This invention is a neural prosthetic apparatus and method for artificially restoring the ability to volitionally cough in a higher level spinal cord injured individual.

2. Description of Prior Art

Pulmonary complications presently account for the majority of morbidity and morality of spinal cord injured individuals. Polatty, R. Crystal, M. D. et al., *Pulmonary Complications in the Spinal Cord Injury Patient*, Physical Medicine and Rehabilitation, Vol. 1, No. 3, p. 353-373, August 1987; and Reines, H. David, M. D. et al., *Pulmonary Complications of Acute Spinal Cord Injuries*, Neurosurgery, Vol. 21, No. 2, p. 193-196, 1987. Two elements contribute to the high incidence of pulmonary morbidity in patients with acute spinal cord injuries. First, there is a restrictive effect of spinal cord injury on pulmonary function, and second, there is morbidity associated with immobilization required in the management of these injuries as well as the diminished active mobility. Retention of secretions, atelectasis, and pneumonia are the most commonly occurring complications and can lead to premature death.

Individuals with cervical spinal cord injuries are frequently impaired in their ability to cough. This deficit has traditionally been approached with the conventional assistive cough that requires physical assistance from a caregiver. Kirby, Nell A., R.N. et al., *An Evaluation of Assisted Cough in Quadriparetic Patients*, Archives of Physical Medicine & Rehabilitation, Vol. 47, p. 705-710, 1966; and Braun, Sheldon R., M.D. et al., *Improving the Cough in Patients with Spinal Cord Injury*, American Journal of Physical Medicine, Vol. 63, No. 1, p. 1-10, 1984. It is likely that under these circumstances, the frequency of coughing in these individuals is reduced, Inability to cough is primarily due to paralysis of abdominal muscles.

This invention for cough assist should not be confused with conventional apparatuses or methods for phrenic pacing. Phrenic pacing is intended to cause contraction of the diaphragm, the major muscle of inspiration. The method and apparatus of this invention causes contraction of the major muscles of expiration, such as abdominal muscles. Phrenic pacing requires an invasive procedure, Glenn, William W. L. et al., *Twenty Years of Experience in Phrenic Nerve Stimulation to Pace the Diaphragm*, Pace, Vol. 9, p. 780-784, November-December 1986, Part I, although percutaneous alternatives, Peterson, D. K. et al, *Intramuscular Electrical Activation of the Phrenic Nerve*, IEEE Transactions on Biomedical Engineering, Vol. BME-33, No. 3, p. 342-351, March 1986, and surface alternatives, Geddes, L. A. et al., *Electroventilation*, American Journal of Emerg. Med., Vol. 3(4), p. 337-339, July 1985, have been proposed. One preferred embodiment of this invention is based on surface electrodes. Depending upon the success or problems with clinical application, a percutaneous or implant system may also be an effective way of stimulating the abdominal muscles for cough assist. Phrenic pacing and artificially stimulated cough reflex address two distinct problems, ventilation and coughing, respectively.

Linder, U.S. Pat. No. 5,190,036, discloses a method and apparatus for stimulating coughing in quadriplegic patients wherein an electrode belt is attached to an abdomen of a patient. At least one electrode of the belt is positioned in close contact with the abdominal area beneath the xiphoid process and costal margins of the patient. A pushbutton switch is momentarily depressed to activate a pulse generator and stimulus pulse circuit. Stimulus pulses are directed from the stimulus pulse circuit to the electrode while the patient is exhaling, so that an electrical stimulus is delivered to the abdominal area of the patient thereby increasing intrathoracic pressures to produce coughing by the patient. The pulse trains are of specified duration and frequency and have specified amplitudes and pulse widths. U.S. Pat. No. 5,190,036 does not teach or suggest an apparatus or method that alerts the patient of an upcoming cough so that the patient can coordinate a volitional activity, particularly after an adjustable time delay, in order to assist the apparatus and thus complete the cough. Furthermore, U.S. Pat. No. 5,190,036 does not teach or even suggest sensing and computing, as a function of a physical and temporal status of a cough and as a function of the current volitional activity of the user, an optimal time for producing a pulse electrical voltage to maximize an air flow rate of the cough.

There is an apparent need for an apparatus and method that enables a quadriplegic patient to initiate an artificially stimulated cough reflex and then to coordinate a volitional activity to complete the cough.

SUMMARY OF THE INVENTION

It is one object of this invention to provide a method and apparatus for artificially stimulating a cough reflex by creating a pulse electrical voltage across a pair of electrodes that electrically stimulate the lower motor neurons, for contracting abdominal muscles.

It is another object of this invention to provide a method and apparatus for artificially stimulating a cough reflex which enables a quadriplegic patient to coordinate and complete a volitional activity after the patient initiates an artificially stimulating cough reflex.

It is another object of this invention to provide a method and apparatus for artificially stimulating a cough reflex wherein an applied pulse electrical voltage across electrodes can be accurately timed as a function of a physical and temporal status of the cough and a volitional activity by the user, which can be sensed and calculated to maximize an air flow rate of the cough.

This invention allows a quadriplegic individual with impaired cough to voluntarily produce electrically stimulated coughs without a caregiver's immediate assistance. The above and other objects of this invention are accomplished with an artificial cough reflex apparatus that includes one or more pairs of electrodes. A stimulator electronically receives an input signal, which is initiated by a user and generates an output signal. By computing the input signal and a stimulus pulse signal generated by an oscillator, the computed output signal can be transformed into a pulse electrical voltage across each pair of electrodes or any selected pair of electrodes. Such pulse electrical voltage activates the lower motor neurons and thereby contracts abdominal muscles.

The apparatus of this invention is preferably used to perform one preferred method of this invention for artificially inducing a cough by positioning each pair of electrodes at or near abdominal muscles. The input signal is then generated, preferably by an electromechanical pushbutton switch or by a transmitter and receiver apparatus. The stimulus pulse signal is generated by an oscillator or by any other suitable pulse signal generating means known to those skilled in the art. The output signal, which is computed from the input signal and the stimulus pulse signal, is emitted from a logic computer and transformed into a pulse electrical voltage which appears across each pair of electrodes. The pulse electrical voltage activates the lower motor neurons and thereby contracts the abdominal muscles those lower motor neurons innervate to produce the cough. The pulse electrical voltage can be produced at an optimal time for maximizing air flow of the cough.

According to one preferred embodiment of this invention, surface electrodes are used to deliver stimulation to abdominal muscles. In another preferred embodiment, surgically implantable electrodes are used. A preferred stimulator of this invention can be clipped onto the waistband of the individual's garment. The stimulator can be triggered by depressing a pushbutton switch, for example for one second. According to one preferred embodiment of this invention, the stimulator beeps, then after a set time delay the apparatus delivers a pulse train to the abdominal muscles and thus initiates the cough. The stimulator can also be programmed so that if the command pushbutton switch is held down for more than four seconds, for example, an alarm signal is produced, indicating that the individual requires assistance from a caregiver.

In other preferred embodiments according to this invention, either a vibrator, a sensory stimulator, or a speech output device can be used to indicate the onset of muscle stimulation in order to alert the user that it is time to initiate the volitional activity. The air flow rate of the cough can be maximized by sensing a physical parameter of the user, such as the current air flow rate of the cough, a pressure of the cough, or a chest or abdominal wall movement, or by using an electromyogram, and then by calculating an optimum time to apply a pulse electrical voltage across the electrodes.

Thus, in order to reduce pulmonary complications, particularly those experienced by quadriplegic individuals, it is apparent that there is a need for a method and apparatus for eliciting a physiologically significant cough reflex. Furthermore, independence from caregivers is a hallmark of effective rehabilitation in nearly every case.

BRIEF DESCRIPTION OF THE DRAWINGS

The above and other objects of this invention will become more apparent to those skilled in the art when the description of this invention is taken in conjunction with the drawings wherein.

DESCRIPTION OF PREFERRED EMBODIMENTS

The muscles of the trunk and abdomen participate in two distinct functions, one of movement and posture, and the second of respiration. In an individual having a spinal cord injury, the function of some or all of these muscles may be lost, leading to deficits in both postural stability and respiration. An ideal outcome of acute management and rehabilitation of such patients would be complete recovery of these functions.

Within the human body, it is well known that when the upper motor neurons within the brain are actuated they transmit action potentials which travel down the spinal cord and excite the lower motor neurons when a muscle movement, such as an abdominal muscle movement, is desired. The action potentials travel down the peripheral nerve and cross the neuromuscular junction, which results in a muscle contraction in the abdominal area.

In upper motor neuron paralysis, the path from the upper motor neurons to the lower motor neurons is severed. Thus, the action potential signal cannot be communicated to the lower motor neurons and the abdominal muscles cannot be voluntarily contracted. However, in the case of upper motor neuron paralysis, the abdominal muscles can be contracted if the lower motor neurons are stimulated electrically, according to this invention.

In the case of lower motor neuron paralysis, the nerves of the lower motor neurons are severed between the lower motor neurons and the abdominal muscle, which results in the abdominal muscles being denervated. In the case of lower motor neuron paralysis, the abdominal muscles cannot be voluntarily contracted or even electrically stimulated for contraction. Thus, the method and apparatus of this invention cannot be used to electrically stimulate the abdominal muscles of an individual having lower motor neuron paralysis.

In cases where potential users, of an apparatus according to this invention, have partial or complete sensation of the skin to electrical stimulation with surface electrodes, such stimulation may cause pain and thus deter use of such apparatus due to user discomfort. In such cases, the pain and discomfort can be significantly reduced or eliminated by using percutaneous or implanted electrodes, as opposed to surface electrodes.

Figure 1:
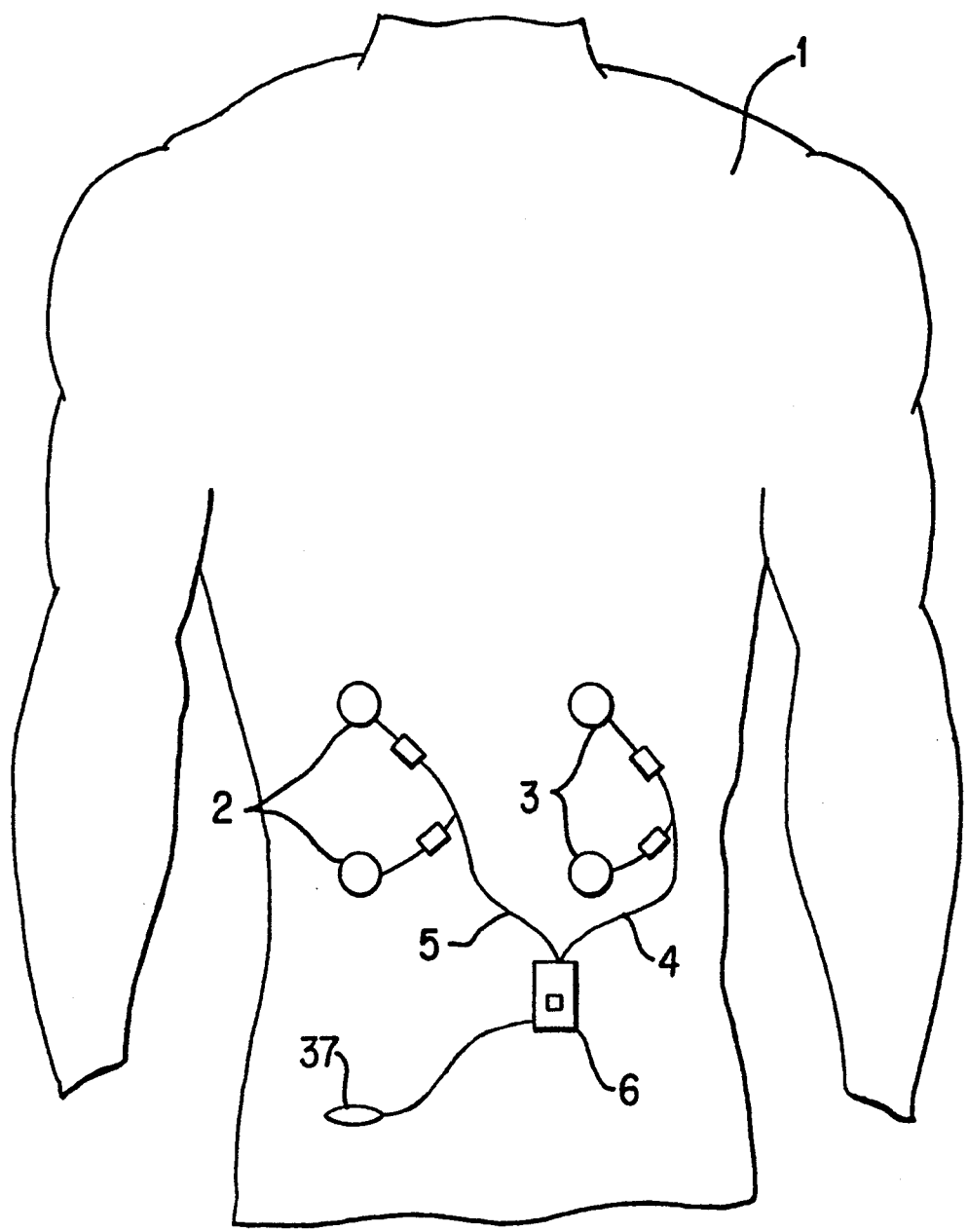
FIG. 1 is a schematic diagram showing the general position of electrodes, cables, a sensor and a stimulator, with respect to an individual's body, according to one preferred embodiment of this invention.

Referring to FIG. 1, an upper body portion of user 1 is shown. According to one preferred embodiment of this invention, the artificial cough reflex apparatus comprises at least one pair of electrodes 14, two pairs of which are schematically shown in FIG. 1 at electrode positions 2, 3. Stimulator means 6 are used to electronically receive an input signal and generate an output signal. Input means are used to generate the input signal and emit such input signal to stimulator means 6. As shown in FIG. 1, stimulator means 6 can be positioned near the waistline of user 1. It is apparent that clip 8, as shown in FIG. 2, or any other suitable securement means can be used to affix or attach stimulator means 6, with respect to the garments worn by user 1 or with respect to the body of user 1.

Figure 2:
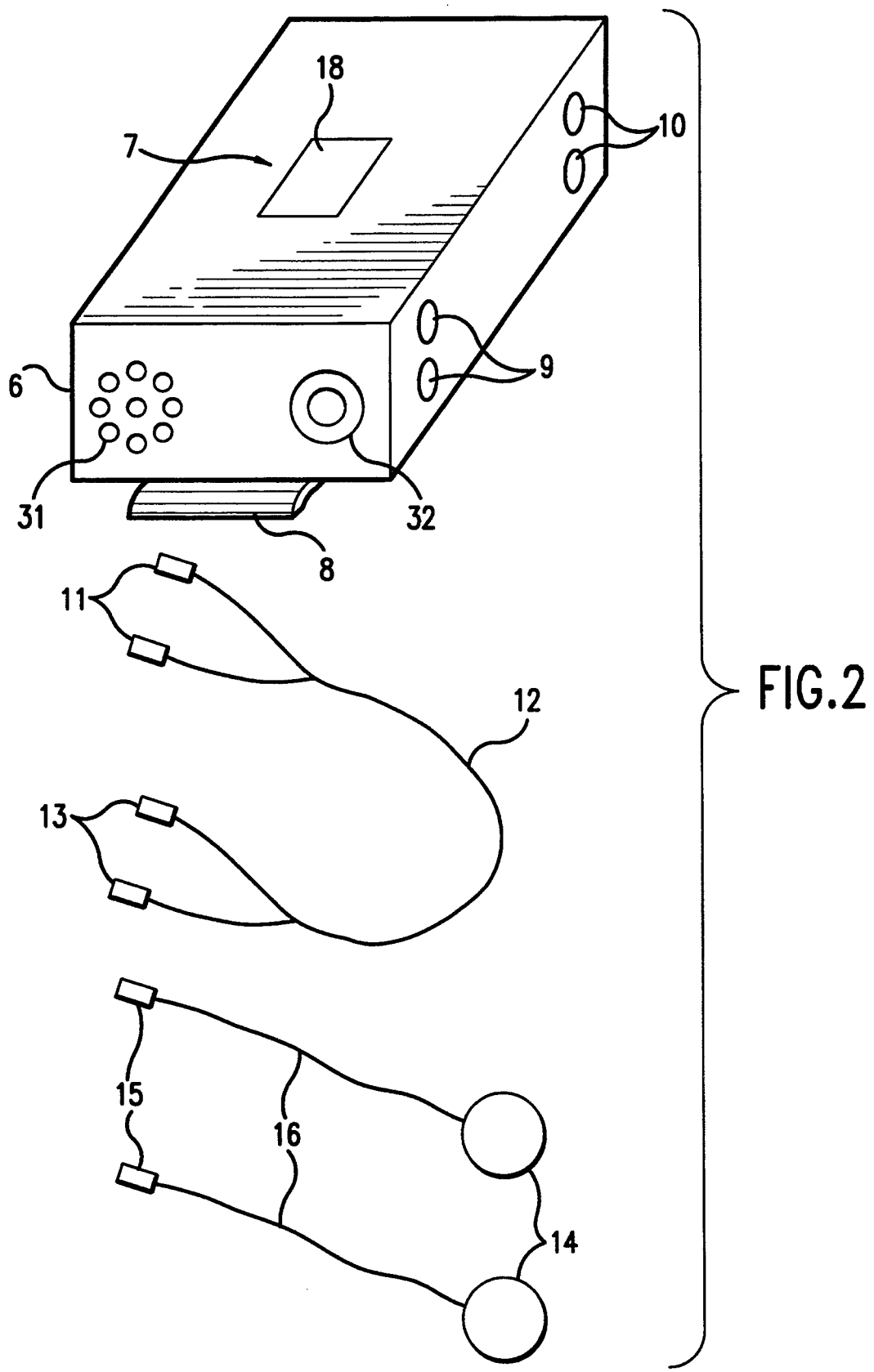
FIG. 2 is an exploded diagrammatic view of a stimulator, cables and electrodes, according to another preferred embodiment of this invention.

According to one preferred embodiment of this invention, the input means comprise sensor 7, such as a pushbutton switch 18 as shown in FIG. 2, connected to stimulator means 6. It is apparent that sensor 7 can be an electro-mechanical pushbutton switch or any other suitable electronic or electro-mechanical switch. In another preferred embodiment according to this invention, the input means comprise transmitter means for selectively transmitting a frequency signal to stimulator means 6. It is apparent to those skilled in the art that a suitable transmitter and receiver apparatus which operates on a radio frequency or any other suitable frequency can be used to transmit the input signal from user 1 to stimulator means 6.

Figure 3:
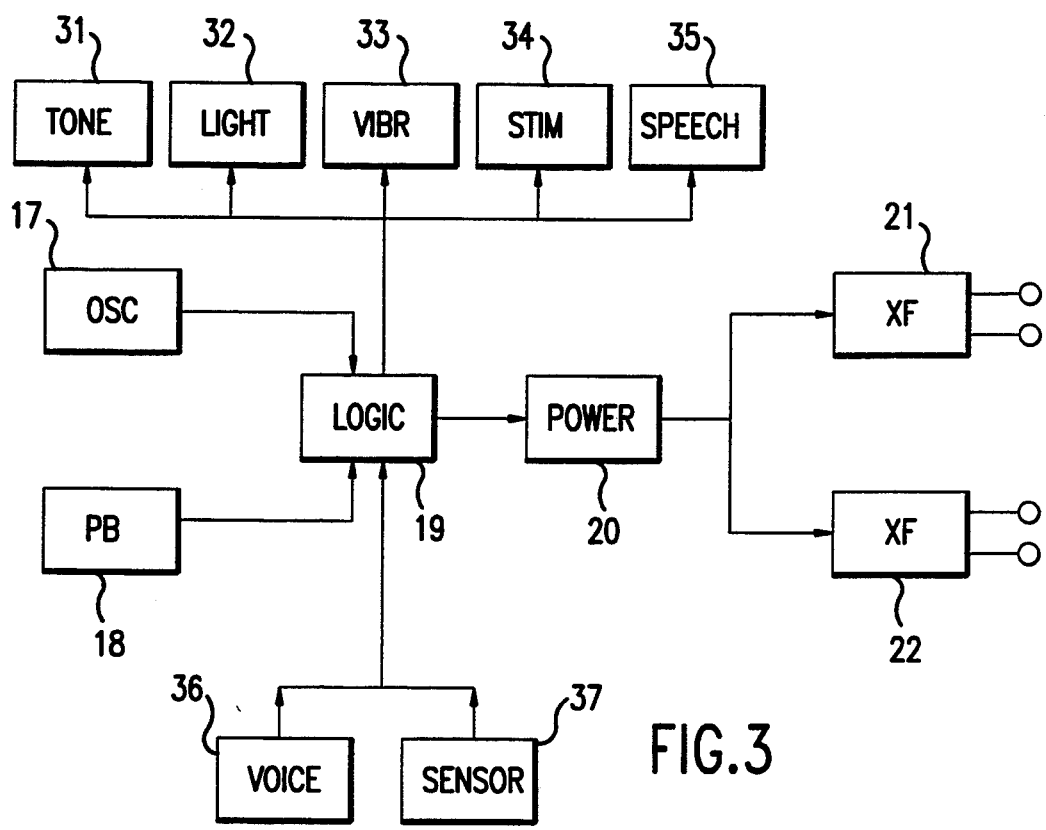
FIG. 3 is a schematic block diagram of a stimulator, according to one preferred embodiment of this invention.

In another preferred embodiment according to this invention, voice activation means 36, as shown in FIG. 3, can be used to activate the input signal upon detection of a particular voice command of user 1. Thus, when user 1 is ready to initiate an assisted cough, a simple voice-activated sensor can be used to initiate the cough.

According to another preferred embodiment of this invention, as shown in FIG. 3, signal means comprise tone 31, light 32, vibration means 33, stimulation means 34 and/or speech activation means 35, any one or more of which can be used to indicate the onset of muscle stimulation to alert user 1 to initiate a volitional activity. It is apparent that any other suitable signalling device can be used to alert user 1 of a precise time that an upcoming cough will occur.

According to another preferred embodiment of this invention as shown in FIG. 3, stimulator means 6 comprise oscillator 17 which is used to produce a selected stimulus pulse signal. It is apparent that other suitable electronics known to those skilled in the art can be used to generate a stimulus pulse signal which is emitted to logic circuit 19, also as shown in FIG. 3. Logic circuit 19 preferably comprises logic computer means for receiving and computing the input signal and the stimulus pulse signal and responsively emitting a computed logic signal to power amplifier 20.

Power amplifier 20 amplifies the computed logic signal and emits such amplified, computed logic signal to pulse transformer 21, 22. Pulse transformer 21, 22 preferably delivers a voltage of approximately 80-150 VDC. The voltage required to elicit a physiologically significant cough reflex is a function of electrode position 2, 3 on the body of user 1, and of the body composition of user 1. It is apparent that depending upon the particular bodily characteristics of user 1, a greater or lesser voltage may be necessary to effectively elicit such physiologically significant cough reflex. According to one preferred embodiment of this invention, stimulator means 6 would also contain a battery as the power source which delivers 12 VDC, for example. Although such battery is portable and more convenient, it is apparent that other suitable and patient-safe power sources known to those skilled in the art can be used in lieu of pulse transformer 21, 22, in order to supply the appropriate pulse voltage across electrodes 14.

According to one preferred embodiment of this invention, electrode 14 is a surface contact electrode which is adhered to the surface skin of user 1 with a suitable adhesive known to those skilled in the art. In another preferred embodiment according to this invention, electrode 14 is a surgically implantable electrode which can be surgically implanted. Such surgically implantable electrodes are known to those skilled in the art. In still another preferred embodiment, electrode 14 is a percutaneously insertable electrode. It is apparent that electrode 14 may comprise any other suitable type of electrode known to those skilled in the art.

Electrodes 14 are electrically connected with stimulator means 6 through cables 4, 5 as shown in FIG. 1, and cables 12 and lead wires 16 as shown in FIG. 2. As shown in FIG. 2, stimulator means 6 has receptacle jacks 9, 10 into which plugs 11 can be inserted. At an opposite end of cable 12, receptacle jacks 13 mate with plugs 15 to form the electrical connection between stimulator means 6 and electrodes 14. It is apparent that a reversal of roles between the receptacle jacks and the plugs or any other suitable electrical connection, including a transmitter and receiver arrangement, can be used to connect electrodes 14 with stimulator means 6.

According to one preferred embodiment of this invention, oscillator 17 produces a desired stimulus pulse signal having pulse width of approximately 300 microseconds, at a frequency of approximately 50 Hertz.

In another preferred embodiment according to this invention, sensor means 37, as shown in FIG. 3, can be used to calculate an optimal time as a function of a physical status and/or temporal status of the cough, as well as the current volitional activity of user 1. The pulse electrical voltage differential can be produced at such optimal time in order to maximize an air flow rate of the cough. The physical and/or temporal status sensed by sensor means 37 can be parameters such as the air flow rate of the cough, the pressure of the cough, or a chest or abdominal wall movement of user 1. An electromyogram can also be used to provide data related to the physical and/or temporal status. It is apparent that other physical parameters can be used to detect the optimal time for producing the pulse electrical voltage and thus effecting the assisted cough.

Figure 4:
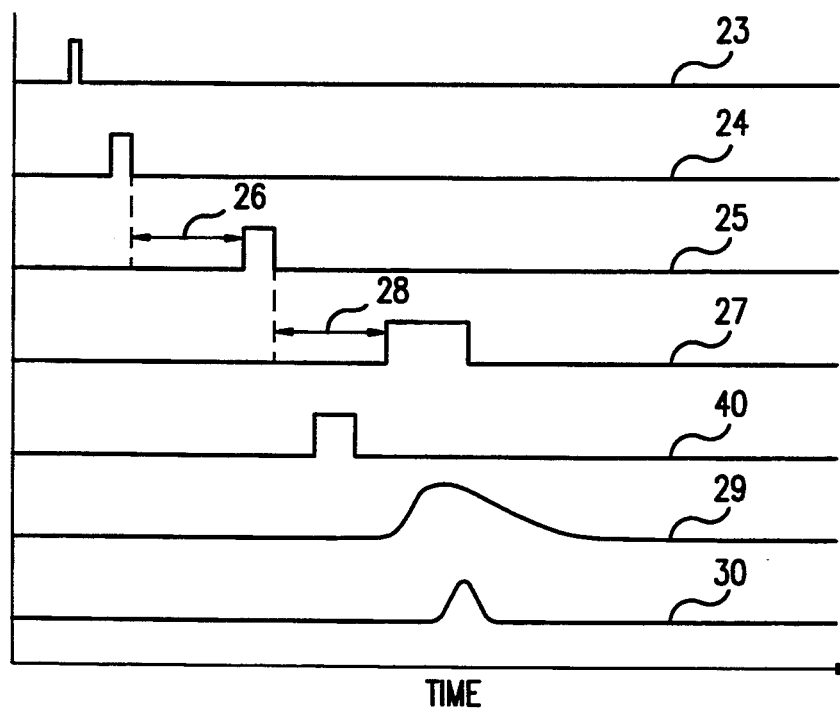
FIG. 4 is a series of events shown in graphic form, according to one preferred method of this invention.

Referring to FIG. 4, certain events for eliciting a physiologically significant cough reflex are shown in graphic form, over time. Trace 23 shows a volitional decision of user 1 to initiate a cough. Trace 24 shows activation of sensor 7, or another suitable input means. Signal 25 can be tone 31 from a speaker or a light 32, as shown in FIGS. 2 and 3. As shown in FIG. 3, it is also apparent that signal 25 can be produced by vibration means 33, such as an electromechanical vibrator, sensory stimulation means 34, or activation means 35, such as a speech activated message, which can be used to indicate the onset of muscle stimulation to alert user 1 to initiate the volitional activity. Signal 25 is preferably produced after the input means are engaged in order to alert user 1 to initiate the volitional activity for assisting an upcoming cough. After variable time delay 26, stimulator means 6 computes and delivers a stimulation which is shown as trace 27. The stimulus pulse signal occurs over a time period shown by 28, in FIG. 4. Sensor trigger output 40 can be used before the abdominal muscles begin to contract for the purpose of timing such contraction at an optimal time which maximizes the air flow rate of the cough. After delivery of the pulse electrical voltage across electrodes 14, the abdominal muscles begin to contract, as shown by trace 29, and the airflow of the cough results at the mouth of user 1, as shown by trace 30.

Referring to FIG. 3 and according to one preferred embodiment of this invention, the method for artificially inducing a cough begins with positioning at least one pair of electrodes 14 about a plurality of abdominal muscles, as shown in FIG. 1 by electrode positions 2, 3. It is apparent that electrodes 14 can be moved into different positions which may result in different forces and thus different airflows for the cough.

Sensor means 37, as shown in FIG. 3, can be used to sense the physical parameters of user 1 and can also comprise computing means for calculating an optimal time, as a function of the physical and/or temporal status of the cough and the volitional activity of user 1. The pulse electrical voltage can then be produced at such optimal time and thus maximize the air flow rate of the cough.

Once electrodes 14 are positioned and either adhered to the surface skin of user 1, or either surgically implanted or percutaneously inserted within or near the abdominal muscles of user 1, an input signal is generated, which is preferably initiated by user 1 as previously discussed. Oscillator 17 or other suitable pulse generation means are used to generate a stimulus pulse signal. Stimulator means 6 then compute the input signal and the stimulus pulse signal and emit an output signal.

The output signal is then transformed into a pulse electrical voltage by either pulse transformer 21, 22 or a DC/DC converter, across each pair of electrodes 14. Such pulse electrical voltage, preferably in a range of about 80–150 VDC, activates the lower motor neurons and thereby contracts the abdominal muscles within user 1, all of which can be optimally timed for producing maximum air flow rate of the cough.

EXAMPLE I

In one particular experiment performed according to this invention, a therapist administered assistive coughs to an individual, and the respiratory measure, peak expiratory force (PEF) was first made without assistance, then with assistance, and finally, with electrical stimulation according to this invention. Five measures within each group were made, and the average for each condition was computed. The raw measurements were analyzed using analysis of variance.

Positive expiratory force was measured with a "Boehringer Model 4100" inspiratory/expiratory manometer. A "Grass Electrophysiological Stimulator (Model S-88)" with a stimulus isolation unit was used. Self-adhering surface electrodes were applied to the skin surface of the individual, near the abdominal muscles. The subject took an inspiration, and indicated he was ready for the stimulation. A light signaled the onset of muscle stimulation. The subject then closed the airway until sufficient pressure was reached, then released the cough. Initially, stimulus pulse trains at 50 Hz, 0.2 msec pulse width, and 0–150 volts amplitude were applied to elicit rapid and forceful contraction of the abdominal muscles.

The raw data and results of the analysis of variance are given below. There was a significant difference between the three groups: controlled; stimulated; assisted.

| GROUP | PEAK EXPIRATORY FORCE (cmH$_2$O) | | |
|---|---|---|---|
| | ASSISTED 1 | ALONE 2 | STIMULATED 3 |
| TRIALS | | | |
| 1 | 44 | 10 | 20 |
| 2 | 30 | 11 | 20 |
| 3 | 36 | 10 | 25 |
| 4 | 30 | 10 | 20 |
| 5 | 30 | | 22 |
| sum | 170 | 41 | 107 |
| "n" | 5 | 4 | 5 |
| avg | 34.00 | 10.25 | 21.40 |
| ANOVA TABLE | Sum Sqs | Deg Fr | Variance | F |
| Between Groups | 2169.800 | 2 | 1084.900 | 82.022 |
| Within Groups | 171.950 | 13 | 13.227 | |
| TOTALS | 2331.750 | 15 | | |

This value of F indicates a statistically significant difference between groups. Further post hoc tests indicated that Group 2 is different from Groups 3 and 1 and that Group 3 is different than Group 1.

EXAMPLE II

Ten quadriplegic patients were studied to test the effectiveness of augmenting the cough by electrically stimulating the abdominal muscles. Peak expiratory flow was measured with a flowmeter during voluntary, assistive, and electrically stimulated coughs. Acceptable abdominal muscle contractions were obtained in five of the ten patients. Sensation to the stimulation precluded use of the technique in four patients, and atrophied abdominal muscles appeared to be a problem in two patients. The three types of coughs were alternately measured for five repetitions. Data from subjects with abdominal muscles that responded to stimulation were analyzed with an analysis of variance, after normalizing flows to the mean flow for volitional coughs. There was a significant difference between the three types of cough, and post hoc comparisons found the means of all three groups to differ. The means of peak expiratory flow in liters per minute ± one standard deviation were: 228±55 (voluntary); 242±48 (stimulated); and 255±42 (assisted).

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

We claim:

1. An artificial cough reflex apparatus comprising:
   at least one pair of electrodes, stimulator means for electronically receiving an input signal and computing an output signal corresponding to a stimulus time period, input means for generating said input signal as a representation of a volitional decision of a user to initiate a cough, signal means for alerting said user of an upcoming said cough, said stimulator means emitting said output signal after an adjustable time delay during which said user coordinates a volitional activity, transformer means for transforming said output signal into a pulse electrical voltage across each said pair of electrodes that activates lower motor neurons and contracts a plurality of expiratory muscles, said signal means for signalling said user to engage said volitional activity and complete said cough, and sensor means for calculating an optimal time as a function of a physical and temporal status of said cough and said volitional activity and for producing said pulse electrical voltage at said optimal time to maximize an air flow rate of said cough.

2. An artificial cough reflex apparatus according to claim 1 wherein said signal means emit an audible tone for indicating an onset of muscle stimulation to alert said user to initiate said volitional activity.

3. An artificial cough reflex apparatus according to claim 1 wherein said signal means comprise a light for indicating an onset of muscle stimulation.

4. An artificial cough reflex apparatus according to claim 1 wherein said signal means comprise vibration means for indicating an onset of muscle stimulation to alert said user to initiate said volitional activity.

5. An artificial cough reflex apparatus according to claim 1 wherein said signal means comprise stimulation means for applying a low level electrical stimulation to an innervated skin area of said user to alert said user to initiate said volitional activity.

6. An artificial cough reflex apparatus according to claim 1 wherein said signal means comprise production means for sounding a stored speech message to alert said user to initiate said volitional activity.

7. An artificial cough reflex apparatus according to claim 1 wherein said stimulator means further comprise logic computer means for receiving said input signal and computing and responsively emitting a computed logic signal.

8. An artificial cough reflex apparatus according to claim 7 wherein said stimulator means further comprise amplification means for amplifying and emitting said computed logic signal to said transformer means.

9. An artificial cough reflex apparatus according to claim 1 wherein said input means comprise an electromechanical pushbutton switch.

10. An artificial cough reflex apparatus according to claim 1 wherein said input means comprise transmitter means for selectively transmitting a frequency signal to said stimulator means.

11. An artificial cough reflex apparatus according to claim 1 wherein said input means comprise activation means for activating said input signal upon detection of a voice command.

12. A method for artificially inducing a cough, including the steps of:
 (a) positioning at least one pair of electrodes about a plurality of abdominal muscles;
 (b) generating an input signal representing a volitional decision of a user to initiate the cough;
 (c) generating a signal to alert said user of an upcoming said cough;
 (d) emitting a computed output signal after an adjustable time delay during which said user coordinates a volitional activity;
 (e) transforming said output signal into a pulse electrical voltage across each said pair of electrodes;
 (f) activating lower motor neurons and thereby contracting said abdominal muscles;
 (g) signalling said user to engage said volitional activity and complete said cough;
 (h) calculating an optimal time as a function of a physical and temporal status of the cough and said volitional activity; and
 (i) producing said pulse electrical voltage at said optimal time to maximize air flow of the cough.

13. A method according to claim 12 wherein each said electrode is positioned on an outer skin layer near said abdominal muscles.

14. A method according to claim 12 wherein each said electrode is surgically implanted within a body near said abdominal muscles.

15. A method according to claim 12 wherein each said electrode is percutaneously inserted within a body near said abdominal muscles.

16. A method according to claim 12 wherein said output signal is an amplified computed logic signal derived from computing an input signal and said stimulus pulse signal.

17. A method according to claim 12 further including the step of transmitting a selected frequency to a receiver that converts said selected frequency into said input signal.

* * * * *